(12) United States Patent
Dakka et al.

(10) Patent No.: US 9,586,898 B2
(45) Date of Patent: Mar. 7, 2017

(54) OXIDATION OF CYCLOHEXYLBENZENE

(75) Inventors: Jihad Mohammed Dakka, Whitehouse Station, NJ (US); Francisco Manuel Benitez, Cypress, TX (US); Bryan Amrutlal Patel, Arlington, VA (US); Edmund John Mozeleski, Califon, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 207 days.

(21) Appl. No.: 13/819,951

(22) PCT Filed: Aug. 16, 2011

(86) PCT No.: PCT/US2011/047843
§ 371 (c)(1),
(2), (4) Date: May 13, 2013

(87) PCT Pub. No.: WO2012/036825
PCT Pub. Date: Mar. 22, 2012

(65) Prior Publication Data
US 2014/0148569 A1 May 29, 2014

Related U.S. Application Data

(60) Provisional application No. 61/489,401, filed on May 24, 2011, provisional application No. 61/382,776, filed on Sep. 14, 2010.

(51) Int. Cl.
| C07C 409/14 | (2006.01) |
| C07C 2/74 | (2006.01) |
| C07C 37/08 | (2006.01) |
| C07C 45/53 | (2006.01) |
| C07C 407/00 | (2006.01) |
| C07C 45/32 | (2006.01) |
| C07C 51/00 | (2006.01) |
| C07C 249/04 | (2006.01) |
| C07D 201/02 | (2006.01) |
| C08G 69/00 | (2006.01) |

(52) U.S. Cl.
CPC .............. *C07C 409/14* (2013.01); *C07C 2/74* (2013.01); *C07C 37/08* (2013.01); *C07C 45/32* (2013.01); *C07C 45/53* (2013.01); *C07C 51/00* (2013.01); *C07C 249/04* (2013.01); *C07C 407/00* (2013.01); *C07D 201/02* (2013.01); *C08G 69/00* (2013.01); *C07C 2101/14* (2013.01); *Y02P 20/52* (2015.11)

(58) Field of Classification Search
CPC .......... C07C 37/08; C07C 39/04; C07C 45/53; C07C 2101/01; C07C 409/14
USPC .................................................. 568/570, 342
See application file for complete search history.

(56) References Cited

U.S. PATENT DOCUMENTS

| 3,846,499 A | 11/1974 | Riedl |
| 6,037,513 A | 3/2000 | Chang et al. |
| 6,720,462 B2 | 4/2004 | Kuhnle et al. |
| 6,852,893 B2 | 2/2005 | Kuhnle et al. |
| 7,038,089 B2 | 5/2006 | De Frutos Escrig et al. |
| 7,326,815 B2 | 2/2008 | Dakka et al. |
| 7,799,956 B2 | 9/2010 | Cheng et al. |
| 2003/0083527 A1 | 5/2003 | Kuhnle et al. |
| 2007/0167658 A1 | 7/2007 | Onuma et al. |
| 2007/0265476 A1 | 11/2007 | Dakka et al. |
| 2008/0086018 A1 | 4/2008 | Cheng et al. |

FOREIGN PATENT DOCUMENTS

| JP | 2002-282698 | 10/2002 |
| WO | 2005/085191 | 9/2005 |
| WO | 2009/025939 | 2/2009 |
| WO | 2009/038900 | 3/2009 |
| WO | WO-2009134514 A | * 11/2009 |
| WO | 2010/074779 | 7/2010 |
| WO | 2010/098916 | 9/2010 |

OTHER PUBLICATIONS

Arends et al., "*Selective catalytic oxidation of cyclohexylbenzene to cyclohexylbenzene-1-hydroperoxide: a coproduct-free route to phenol,*" Tetrahedron (58), pp. 9055-9061 (2002).
Yen, Y., "*Phenol,*" Process Economics Report No. 22B, Stanford Research Institute, pp. 113-124, 261 and 263 (1977).

* cited by examiner

*Primary Examiner* — Sudhakar Katakam
*Assistant Examiner* — Ana Z Muresan
(74) *Attorney, Agent, or Firm* — Stephen A. Baehl

(57) ABSTRACT

In a process for oxidizing a feed comprising cyclohexylbenzene, the feed is contacted with oxygen and an oxidation catalyst in a plurality of reaction zones connected in series, the contacting being conducted under conditions being effective to oxidize part of the cyclohexylbenzene in the feed to cyclohexylbenzene hydroperoxide in each reaction zone. At least one of the plurality of reaction zones has a reaction condition that is different from another of the plurality of reaction zones. The different reaction conditions may include one or more of (a) a progressively decreasing temperature and (b) a progressively increasing oxidation catalyst concentration as the feed flows from one reaction zone to subsequent reaction zones in the series.

22 Claims, No Drawings

OXIDATION OF CYCLOHEXYLBENZENE

PRIORITY CLAIM

This application is a National Stage Application of International Application No. PCT/US2011/047843 filed Aug. 16, 2011, which claims priority to and the benefit of U.S. Provisional Application Ser. No. 61/489,401 filed May 24, 2011 and 61/382,776 filed Sep. 14, 2010, both of which are incorporated herein by reference in their entirety.

CROSS REFERENCE TO RELATED APPLICATIONS

This application is related to U.S. App. Ser. No. 12/678,419; and U.S. Prov. Nos. 61/424,229; and 61/468,290.

FIELD

The present invention relates to a process for oxidizing cyclohexylbenzene and, in particular, to a process for oxidizing cyclohexylbenzene and then cleaving the resultant cyclohexylbenzene hydroperoxide to produce phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process involving alkylation of benzene with propylene to produce cumene, followed by oxidation of the cumene to the corresponding hydroperoxide, and then cleavage of the hydroperoxide to produce equimolar amounts of phenol and acetone.

Another process involves the catalytic hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts. Such a process is described in, for example, U.S. Pat. No. 6,037,513, in which the hydroalkylation catalyst is a bifunctional catalyst comprising at least one hydrogenation metal and a molecular sieve of the MCM-22 family.

However, one problem in producing phenol via cyclohexylbenzene is that the oxidation of cyclohexylbenzene is considerably more difficult than that of cumene. Thus, whereas cumene oxidation is normally conducted in the absence of a catalyst, cyclohexylbenzene oxidation typically requires the presence of a catalyst containing a nitroxyl radical, particularly a cyclic imide, such as N-hydroxyphthalimide (NHPI), to provide commercially acceptable levels of conversion. Moreover, even using NHPI as a catalyst, the selectivity to cyclohexylbenzene hydroperoxide decreases with increasing conversion. Also, although the oxidation of cyclohexylbenzene is exothermic, the temperature must be controlled within a relatively narrow range if the production of unwanted by-products is to be minimized. Thus, there is significant interest in developing improved methods of oxidizing cyclohexylbenzene that allow for increased yields of the desired hydroperoxide.

According to the present invention, it has now been found that an advantageous combination of high conversion and high selectivity can be achieved in the oxidation of cyclohexylbenzene in the presence of a cyclic imide catalyst by conducting the oxidation in a plurality of series-connected reactors with the temperature being decreased and/or the catalyst concentration being increased from the first to the final reactor.

U.S. Pat. Nos. 6,852,893 and 6,720,462 describe methods for producing phenol by catalytic oxidation of alkylaromatic hydrocarbons to the corresponding hydroperoxide, and subsequent cleavage of the hydroperoxide to give phenol and a ketone. Catalytic oxidation takes place with oxygen, in the presence of a free radical initiator and a catalyst, typically an N-hydroxycarbodiimide catalyst, such as N-hydroxyphthalimide. Preferred alkylaromatic hydrocarbons that may be oxidized by this process include cumene, cyclohexylbenzene, cyclododecylbenzene and sec-butylbenzene.

International Patent Publication No. WO2010/074779 discloses a process for oxidizing an alkylaromatic compound, such as sec-butylbenzene and cyclohexylbenzene, to the corresponding alkylaromatic hydroperoxide by contacting the alkylaromatic compound with oxygen in the presence of a cyclic amide catalyst, such as N-hydroxyphthalimide, which is substantially free of alkali metal compounds. According to this publication, if the oxidation is conducted at a temperature of about 90° C. to about 150° C. with the cyclic imide being present in an amount between about 0.05 wt % and about 5 wt % of the alkylaromatic in the feed, conversion rates of at least 4 wt %/hour can be achieved with a selectivity to the hydroperoxide of at least 90%.

SUMMARY

In one aspect, the invention resides in a process for oxidizing a feed comprising cyclohexylbenzene, the process comprising contacting the feed with oxygen in the presence of an oxidation catalyst in a plurality of reaction zones connected in series, wherein the contacting in at least two of the plurality of reaction zones is conducted under conditions effective to oxidize a portion of the cyclohexylbenzene in the feed to cyclohexylbenzene hydroperoxide, and at least one of the reaction zones has a reaction condition that is different from another of the plurality of reaction zones. In various embodiments, the different reaction condition includes one or more of: (a) a decrease in temperature and (b) an increase in catalyst concentration as the feed flows from one reaction zone to the next reaction zone in the series.

Conveniently, the different reaction condition includes a progressively decreasing temperature between adjacent reaction zones of at least 5° C. In one embodiment, the temperature in the first reaction zone is about 100° C. to about 120° C. and the temperature in the final reaction zone is about 70° C. to about 90° C.

Conveniently, fresh oxidation catalyst is supplied to each reaction zone such that the different reaction condition includes an increase in catalyst concentration as the feed flows from one reaction zone to the next reaction zone in the series.

Conveniently, the oxidation catalyst comprises an imide group having the formula:

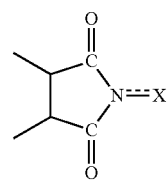

wherein X represents an oxygen atom, a hydroxyl group, or an acyloxy group.

In one embodiment, the oxidation catalyst comprises N-hydroxyphthalimide.

In a further aspect, the invention resides in a process for producing phenol and cyclohexanone, the process comprising:

(i) hydroalkylating benzene with hydrogen in the presence of a hydroalkylation catalyst under conditions effective to produce cyclohexylbenzene;

(ii) contacting a feed comprising at least a portion of the cyclohexylbenzene with oxygen in the presence of a cyclic imide catalyst in a plurality of reaction zones connected in series, wherein the contacting in each reaction zone is conducted under conditions effective to oxidize a portion of the cyclohexylbenzene in the feed to cyclohexylbenzene hydroperoxide, and the reaction zones have at least one different condition, and the different condition is at least one of (a) a decrease in temperature and (b) an increase in catalyst concentration as the feed flows from one reaction zone to the next reaction zone in the series; and (iii) cleaving at least a portion of the cyclohexylbenzene hydroperoxide produced in (ii) to produce phenol and cyclohexanone.

DESCRIPTION

Described herein is a process for producing cyclohexylbenzene hydroperoxide, in which cyclohexylbenzene is contacted with oxygen (e.g., an oxygen-containing gas) in the presence of an oxidation catalyst (e.g., a cyclic imide catalyst) in a plurality of series-connected oxidation reaction zones. By controlling the conditions in the reaction zones so that there is a decrease in temperature and/or an increase in catalyst concentration as the feed flows from one reaction zone to the next reaction zone in the series, it is found that a unique and advantageous combination of high oxidation conversion and high selectivity to the desired hydroperoxide can be achieved.

In one preferred embodiment, the present oxidation process forms part of an integrated process for producing phenol and cyclohexanone from benzene, in which the benzene is converted to cyclohexylbenzene, the cyclohexylbenzene is then oxidized to cyclohexylbenzene hydroperoxide, and the cyclohexylbenzene hydroperoxide is cleaved to produce phenol and cyclohexanone. The present process will therefore be described in relation to this preferred embodiment, although it is to be appreciated that the cyclohexylbenzene hydroperoxide product of the present process can also be used as an oxidant in, for example, the oxidation of hydrocarbons, or as an initiator, in, for example, olefin polymerization.

Production of the Cyclohexylbenzene

The initial step in the present integrated process involves the production of cyclohexylbenzene by reacting benzene with cyclohexene in the presence of a catalyst having an alkylation function and under conditions to promote the following reaction:

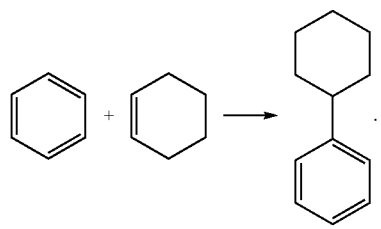

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

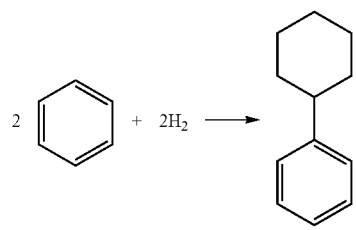

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as, less than 500 ppm, for example, less than 100 ppm, water. In addition, the total feed typically contains less than 100 ppm, such as, less than 30 ppm, for example, less than 3 ppm, sulfur and less than 10 ppm, such as, less than 1 ppm, for example, less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example, at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

Treatment of the Cyclohexylbenzene Product

Although the hydroalkylation reaction using an MCM-22 family zeolite catalyst is highly selective towards cyclohexylbenzene, the liquid effluent from the hydroalkylation reaction will inevitably contain significant quantities of unreacted benzene and certain by-products in addition to the desired cyclohexylbenzene. One of the major by-products are polycyclohexylbenzenes (di- and tricyclohexylbenzene), which typically comprise up to 20 wt % of the conversion products. These polycyclohexylbenzenes may be converted into additional useful cyclohexylbenzene product.

For example, separation of the polycyclohexylbenzenes is conveniently achieved by supplying at least a portion of the reaction product to a fractionation device, normally a fractionation column, to separate the reaction product into at least a first fraction rich in cyclohexylbenzene and a second fraction rich in polycyclohexylbenzenes. In addition, to allow the separation to be effected at or near atmospheric pressure (about 100 kPa to about 300 kPa) and at relatively low temperatures, at least one $C_4$ to $C_6$ hydrocarbon in the vapor phase is supplied separately to the fractionation device, normally at or adjacent the base of the fractionation column. Although any $C_4$ to $C_6$ hydrocarbon vapor can be used, benzene vapor is particularly useful since, for example, the hydroalkylation reaction effluent contains significant quantities (typically up to 60 wt %) of unreacted benzene.

Conveniently, the $C_4$ to $C_6$ hydrocarbon vapor is supplied to the fractionation device at a temperature of about 190° C. to about 300° C. More particularly, where steam is used to heat and vaporize the $C_4$ to $C_6$ hydrocarbon, the temperature of the $C_4$ to $C_6$ hydrocarbon vapor supplied to the fractionation device is between about 190° C. and about 241° C. Generally, the ratio of the weight of the $C_4$ to $C_6$ hydrocarbon vapor supplied to the fractionation device to the weight of the reaction product supplied to the fractionation device is from about 0.05:1 to about 2:1, such as from about 0.1:1 to about 1:1, for example about 0.5:1.

In one embodiment of the present process, after separation from the hydroalkylation reaction effluent, the polycyclohexylbenzenes are mixed with benzene and transalkylated to produce additional monocyclohexylbenzene. Transalkylation is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio 1:1 to about 5:1.

In another embodiment of the present process, conversion of the polycyclohexylbenzenes to additional monocyclohexylbenzene is effected by dealkylation. Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds, and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

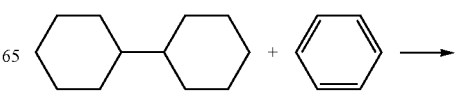

The catalytic treatment can be conducted on the direct product of the hydroalkylation reaction or after distillation of the hydroalkylation reaction product to separate the $C_6$ and/or the heavies fraction.

The cyclohexylbenzene-rich stream separated from the hydroalkylation reaction product is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air.

The oxidation is conducted in the presence of a catalyst and especially an N-hydroxy substituted cyclic imide catalyst as described in U.S. Pat. No. 6,720,462, incorporated herein by reference. Suitable catalysts comprise an imide group having the following formula I:

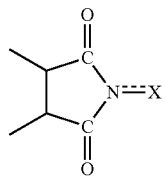

(I)

wherein X represents an oxygen atom, a hydroxyl group, or an acyloxy group.

Generally, the cyclic imide catalyst obeys the general formula II:

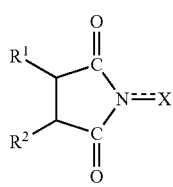

(II)

wherein X represents an oxygen atom, a hydroxyl group, or an acyloxy group and $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may bonded together to form a double bond or an aromatic- or non-aromatic ring.

More specifically, the cyclic imide employed as the oxidation catalyst typically obeys the following general formula (III):

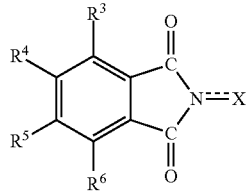

(III)

wherein X represents an oxygen atom, a hydroxyl group and each of $R^3$, $R^4$, $R^5$, and $R^6$ is independently selected from H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I, and/or $NO_2$.

In one practical embodiment, the cyclic imide catalyst comprises N-hydroxyphthalimide or N,N',N"-trihydroxyisocyanuric acid.

The cyclic imide oxidation catalyst can be used either alone or in conjunction with a free radical initiator, and further can be used as a liquid-phase, homogeneous catalyst or can be supported on a solid carrier to provide a heterogeneous catalyst. Typically, the cyclic imide catalyst is employed in an amount between 0.0001 wt % to 15 wt %, such as between 0.001 wt % to 5 wt %, of the cyclohexylbenzene.

The oxidation reaction is conducted in a plurality of reaction zones connected in series, with at least two of the reaction zones conducting a portion of the oxidation reaction. The reaction zones may be part of a single reactor or two or more of the reaction zones may be located in different reactors. One or more oxidation conditions are arranged to be different in each reaction zone. In one embodiment, the reaction conditions are controlled such that there is a decrease in temperature, generally by at least 5° C., or at least 7° C., or at least 10° C., such as from about 5° C. to about 25° C., as the feed flows from one reaction zone to the next reaction zone in the series. Since, the oxidation reaction is exothermic, such a gradual decrease in reaction temperature generally requires cooling of the oxidation effluent between adjacent reaction zones. Typically, the temperature in the first reaction zone is arranged to be about 100° C. to about 120° C., while the temperature in the final reaction zone is about 70° C. to about 90° C. The temperature reduction may be achieved by any conventional method. For example, parallel or counter-flow heat exchangers may be used.

In various embodiments, the conditions in each reaction zone are effective to oxidize at least 1% of the cyclohexylbenzene present.

In another embodiment, different reaction conditions in each reaction zone are achieved by supplying fresh cyclic imide catalyst to each reaction zone so that there is a increase or maintenance (due to NHPI decomposition) of catalyst concentration as the cyclohexylbenzene feed flows from one reaction zone to the next reaction zone in the series. Preferably, the rate of catalyst addition is controlled so that the amount of fresh cyclic imide catalyst supplied to each downstream reaction zone is enough to improve the CHBHP selectivity taking in consideration the limited solubility of the NHPI in CHB/CHBHP mixture. In various embodiments, at least 100 ppmw of fresh cyclic imide catalyst is supplied to the first reaction zone, based upon the weight of the feed entering the reaction zone. Additionally or alternatively, at least 500 ppmw of fresh cyclic imide catalyst may be supplied to the final reaction zone, based upon the weight of the feed entering the reaction zone.

In a further embodiment, the different reaction conditions in each reaction zone include both a decrease in temperature and an increase in catalyst concentration as the feed flows from one reaction zone to the next reaction zone in the series.

In another embodiment, one or more oxidation reactors are connected in parallel with the oxidation reactors that are connected in connected in series. Conveniently, this configuration promotes maintenance on one or more of the reactors without shutting down the process, and/or allows the catalyst to be rejuvenated and/or regenerated.

Purification of the Oxidation Product

Typically, the product of the cyclohexylbenzene oxidation reaction contains at least 5 wt %, such as at least 10 wt %, for example at least 15 wt %, or at least 20 wt % cyclohexylbenzene hydroperoxide based upon the total weight of the oxidation reaction effluent. Generally, the oxidation reaction effluent contains no greater than 50 wt %, or no greater than 40 wt %, or no greater than 30 wt %, or no greater than 25 wt % of cyclohexylbenzene hydroperoxide based upon the total weight of the oxidation reaction effluent. The oxidation reaction effluent further comprises imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

Generally, at least a portion of the oxidation reaction effluent is subjected to purification to remove at least part of the imide catalyst and the unreacted cyclohexylbenzene before passage to the cleavage step. Typically, all or a fraction of the oxidation reaction effluent initially undergoes treatment to reduce the level of the cyclic imide in the effluent to, for example, less than 100 ppmw, such as less than 20 ppmw. This is conveniently effected by contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. Another possible separation involves passage of all or a fraction of the oxidation effluent over a bed of solid sorbent. Suitable solid sorbents include alkali metal carbonates, alkali metal bicarbonates, alkali metal hydroxides, alkali metal hydroxide-carbonate complexes, alkaline earth metal carbonates, alkaline earth metal bicarbonates, alkaline earth metal hydroxides, and alkaline earth metal hydroxide-carbonate complexes. An example of separation of cyclic imide by basic material treatment is disclosed in International Patent Publication No. WO 2009/025939.

After treatment to remove the cyclic imide catalyst, the oxidation effluent is maintained under conditions such that crystals of cyclohexylbenzene hydroperoxide form and separate from the treated reaction product. This is conveniently achieved by cooling the treated reaction product to a temperature between about 2° C. and about 10° C. and allowing the crystals to form, which normally takes from about 2 hours to about 170 hours. When crystallization is complete the cyclohexylbenzene hydroperoxide crystals can be recovered from the oxidation effluent and supplied to the cleavage step. The crystallization step can be performed one time or can be repeated several times to improve the yield of the cyclohexylbenzene hydroperoxide. The recovered cyclohexylbenzene hydroperoxide crystals typically have a purity of >85%, preferably >90%.

Hydroperoxide Cleavage

The final reactive step in the conversion of the cyclohexylbenzene into phenol and cyclohexanone involves the acid-catalyzed cleavage of the cyclohexylbenzene hydroperoxide recovered from the oxidation reaction effluent.

In one embodiment, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm and no greater than 3000 wppm, or at least 150 wppm and no greater than 2000 wppm of the acid catalyst, or at least 300 wppm and no greater than 1500 wppm of the acid catalyst, based upon total weight of the cleavage reaction mixture.

In various embodiments, the cleavage catalyst may be zeolite beta, zeolite Y, ZSM-5 zeolite, ZSM-12 zeolite, and/or mordenite.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less, such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

Suitable cleavage conditions include a temperature of at least 20° C. and no greater than 200° C., or at least 40° C. and no greater than 120° C., and a pressure of at least 1 psig and no greater than 370 psig (at least 7 kPa and no greater than 2,550 kPa, gauge), or at least 14.5 psig and no greater than 145 psig (at least 100 kPa and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction are phenol and cyclohexanone, each of which generally comprises about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

The cleavage reaction product may contain unreacted acid catalyst and hence at least a portion of the cleavage reaction product may be neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide, and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay, such as limestone, dolomite, magnesite, sepiolite, and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium, and radium; an oxide of Group III of the Periodic Table of Elements treated with a metal selected from lithium, potassium, sodium, rubidium, and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate, and sodium carbonate; and amine (s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines, and alkanolamines. In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites, and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 psig to about 500 psig (5 kPa to 3450 kPa, gauge), or about 10 psig to 200 psig (70 kPa to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which can be purified and separated by methods well known in the art.

Uses of Cyclohexanone and Phenol

The cyclohexanone produced through the processes disclosed herein may be used, for example, as an industrial solvent, as an activator in oxidation reactions, and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ϵ-caprolactam, adipic acid, and/or plasticizers.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Additionally or alternately, the invention can be described by the following embodiments:

1. A process for oxidizing a feed comprising cyclohexylbenzene, the process comprising:
   contacting the feed with oxygen and an oxidation catalyst in a plurality of reaction zones connected in series, wherein the contacting in at least two of the plurality of reaction zones is conducted under conditions effective to oxidize a portion of the cyclohexylbenzene to cyclohexylbenzene hydroperoxide, and at least one of the plurality of reaction zones has a different reaction condition than another of the plurality of reaction zones.
2. The process of embodiment 1, wherein the plurality of reaction zones consists of three reaction zones.
3. The process of embodiment 1, wherein the different reaction condition includes a temperature decrease from at least one of the plurality of reaction zones to the next of the plurality of reaction zones in the series.
4. The process of embodiment 1, wherein the different reaction condition includes a temperature decrease of at least 5° C. from at least one of the plurality of reaction zones to the next of the plurality of reaction zones in the series.
5. The process of embodiment 1, wherein the temperature in the first of the plurality of reaction zones in the series is about 100° C. to about 120° C. and the temperature in the last of the plurality of reaction zones in the series is about 70° C. to about 90° C.
6. The process of embodiment 1, wherein the different reaction condition includes an increase in oxidation catalyst concentration in the feed from at least one of the plurality of reaction zones to the next of the plurality of reaction zones in the series.
7. The process of embodiment 1, wherein the different reaction condition includes an increase in oxidation catalyst in the feed of at least 100 ppmw from at least one of the plurality of reaction zones to the next of the plurality of reaction zones in the series.
8. The process of embodiment 1, wherein at least 100 ppmw of the oxidation catalyst is supplied to the first of the plurality of reaction zones in the series, based upon total weight of the feed entering the reaction zone.
9. The process of embodiment 1, wherein at least 500 ppmw of the oxidation catalyst is supplied to the last of the plurality of reaction zones in the series, based upon total weight of the feed entering the reaction zone.
10. The process of embodiment 1, wherein the conditions in at least some of the plurality of reaction zones are effective to oxidize at least 1% of the cyclohexylbenzene present.
11. The process of embodiment 1, wherein at least one of the plurality of reaction zones comprises a continuous stirred-tank reactor (CSTR).
12. The process of embodiment 1, wherein fresh oxidation catalyst is supplied to at least some of the plurality of reaction zones.
13. The process of embodiment 1, wherein the oxidation catalyst comprises a cyclic imide.
14. The process of embodiment 1, wherein the oxidation catalyst comprises an imide group having the formula:

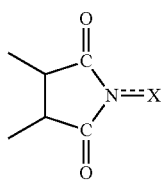

wherein X represents an oxygen atom, a hydroxyl group, or an acyloxy group.
15. The process of embodiment 1, wherein the oxidation catalyst comprises N-hydroxyphthalimide.
16. A process for producing phenol and cyclohexanone, the process comprising:
   (i) hydroalkylating benzene with hydrogen in the presence of a hydroalkylation catalyst under conditions effective to produce cyclohexylbenzene;
   (ii) contacting a feed comprising at least a portion of the cyclohexylbenzene with oxygen in the presence of a cyclic imide catalyst in a plurality of reaction zones connected in series, wherein the contacting in at least some of the plurality of reaction zones is conducted under conditions effective to oxidize a portion of the cyclohexylbenzene to cyclohexylbenzene hydroperoxide, and at least one of the plurality of reaction zones has a different reaction condition than another of the plurality of reaction zones, and the different reaction condition is at least one of (a) a decrease in temperature and (b) an increase in catalyst concentration as the feed flows from one reaction zone to the next reaction zone in the series; and
   (iii) cleaving at least a portion of the cyclohexylbenzene hydroperoxide produced in (ii) to produce phenol and cyclohexanone.
17. The process of embodiment 16, further comprising separating at least a portion of the phenol from the cyclohexanone.
18. The process of embodiment 16, wherein at least a portion of the phenol is converted to at least one of a phenolic resin, bisphenol A, ε-caprolactam, an adipic acid, or a plasticizer.
19. The process of embodiment 16, wherein at least a portion of the cyclohexanone is converted into at least one of adipic acid, a cyclohexanone resin, a cyclohexanone oxime, caprolactam, or nylon.
20. The process of embodiment 16, wherein there is at least one reaction zone connected in parallel with one or more of the plurality of reactors connected in series.
21. The process of embodiment 16, wherein the different reaction condition includes at least one of the plurality of reaction zones having a temperature of at least 5° C. higher than the next of the plurality of reaction zones in the series.
22. The process of embodiment 16, wherein the temperature in the first reaction zone is about 100° C. to about 120° C. and the temperature in the final reaction zone is about 70° C. to about 90° C.
23. The process of embodiment 16, wherein the different reaction condition includes an increase in oxidation catalyst concentration in the feed from at least one of the plurality of reaction zones to the next of the plurality of reaction zones in the series.
24. The process of embodiment 16, wherein the cyclic imide catalyst comprises N-hydroxyphthalimide.
25. The process of embodiment 16, wherein the hydroalkylation catalyst comprises a hydrogenation metal and a zeolite selected from zeolite beta, zeolite X, zeolite Y, mordenite, and a molecular sieve of the MCM-22 family.

The invention claimed is:
1. A process for oxidizing a feed comprising cyclohexylbenzene, the process comprising:
   contacting the feed with oxygen and an oxidation catalyst in a plurality of reaction zones connected in series, wherein the contacting in at least two of the plurality of reaction zones is conducted under conditions effective to oxidize a portion of the cyclohexylbenzene to cyclohexylbenzene hydroperoxide, and at least one of the plurality of reaction zones has a different reaction condition than another of the plurality of reaction zones;
wherein the different reaction condition includes both: (i) a temperature decrease and (ii) an increase in oxidation catalyst concentration in the feed from at least one of the plurality of reaction zones to the next of the plurality of reaction zones in the series.

2. The process of claim 1, wherein the plurality of reaction zones consists of three reaction zones.

3. The process of claim 1, wherein the temperature decrease is at least 5° C.

4. The process of claim 1, wherein the temperature in the first of the plurality of reaction zones in the series is about 100° C. to about 120° C. and the temperature in the last of the plurality of reaction zones in the series is about 70° C. to about 90° C.

5. The process of claim 1, wherein increase in oxidation catalyst concentration in the feed is of at least 100 ppmw from at least one of the plurality of reaction zones to the next of the plurality of reaction zones in the series.

6. The process of claim 1, wherein at least 100 ppmw of the oxidation catalyst is supplied to the first of the plurality of reaction zones in the series based upon total weight of the feed entering the reaction zone.

7. The process of claim 1, wherein at least 500 ppmw of the oxidation catalyst is supplied to the last of the plurality of reaction zones in the series, based upon total weight of the feed entering the reaction zone.

8. The process of claim 1, wherein the conditions in at least some of the plurality of reaction zones are effective to oxidize at least 1% of the cyclohexylbenzene present.

9. The process of claim 1, wherein at least one of the plurality of reaction zones comprises a continuous stirred-tank reactor (CSTR).

10. The process of claim 1, wherein fresh oxidation catalyst is supplied to at least some of the plurality of reaction zones.

11. The process of claim 1, wherein the oxidation catalyst comprises a cyclic imide.

12. The process of claim 1, wherein the oxidation catalyst comprises an imide group having the formula:

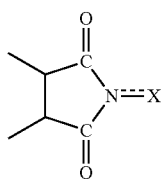

wherein X represents an oxygen atom, a hydroxyl group, or an acyloxy group.

13. The process of claim 1, wherein the oxidation catalyst comprises N-hydroxyphthalimide.

14. A process for producing phenol and cyclohexanone, the process comprising:
hydroalkylating benzene with hydrogen in the presence of a hydroalkylation catalyst under conditions effective to produce cyclohexylbenzene;
(ii) contacting a feed comprising at least a portion of the cyclohexylbenzene with oxygen in the presence of a cyclic imide catalyst in a plurality of reaction zones connected in series, wherein the contacting in at least some of the plurality of reaction zones is conducted under conditions effective to oxidize a portion of the cyclohexylbenzene to cyclohexylbenzene hydroperoxide, and at least one of the plurality of reaction zones has a different reaction condition than another of the plurality of reaction zones, and the different reaction condition comprises both (a) a decrease in temperature and (b) an increase in catalyst concentration as the feed flows from one reaction zone to the next reaction zone in the series; and
(iii) cleaving at least a portion of the cyclohexylbenzene hydroperoxide produced in (ii) to produce phenol and cyclohexanone.

15. The process of claim 14, further comprising separating at least a portion of the phenol from the cyclohexanone.

16. The process of claim 14, wherein at least a portion of the phenol is converted to at least one of a phenolic resin, bisphenol A, ε-caprolactam, an adipic acid, or a plasticizer.

17. The process of claim 14, wherein at least a portion of the cyclohexanone is converted into at least one of adipic acid, a cyclohexanone resin, a cyclohexanone oxime, caprolactam, or nylon.

18. The process of claim 14, wherein there is at least one reaction zone connected in parallel with one or more of the plurality of reactors connected in series.

19. The process of claim 14, wherein the different reaction condition includes at least one of the plurality of reaction zones having a temperature of at least 5° C. higher than the next of the plurality of reaction zones in the series.

20. The process of claim 14, wherein the temperature in the first reaction zone is about 100° C. to about 120° C. and the temperature in the final reaction zone is about 70° C. to about 90° C.

21. The process of claim 14, wherein the cyclic imide catalyst comprises N-hydroxyphthalimide.

22. The process of claim 14, wherein the hydroalkylation catalyst comprises a hydrogenation metal and a zeolite selected from zeolite beta, zeolite X, zeolite Y, mordenite, and a molecular sieve of the MCM-22 family.

* * * * *